(12) United States Patent
Fujiwara

(10) Patent No.: US 7,129,281 B2
(45) Date of Patent: Oct. 31, 2006

(54) ONE-BOTTLE DENTAL BONDING COMPOSITION

(75) Inventor: Satoshi Fujiwara, Otawara (JP)

(73) Assignee: Dentsply-Sankin K.K. (JP)

( * ) Notice: Subject to any disclaimer, the term of this patent is extended or adjusted under 35 U.S.C. 154(b) by 0 days.

(21) Appl. No.: 10/392,256

(22) Filed: Mar. 18, 2003

(65) Prior Publication Data

US 2003/0187092 A1    Oct. 2, 2003

(30) Foreign Application Priority Data

Mar. 19, 2002    (JP) .............................. 2002-076797

(51) Int. Cl.
*C08J 3/28* (2006.01)
*C08J 3/09* (2006.01)
*C08J 3/20* (2006.01)

(52) U.S. Cl. .................. 522/153; 522/76; 522/14; 522/21; 522/33; 522/48; 522/71; 522/82; 522/79; 522/83; 522/104; 522/107; 522/149; 522/150; 522/90; 522/96; 522/154; 522/164; 522/179; 522/178; 522/908; 523/109; 523/115; 523/116; 523/118; 523/300

(58) Field of Classification Search .................. 522/76, 522/14, 21, 33, 48, 71, 82, 79, 83, 104, 107, 522/149, 150, 90, 96, 153, 154, 164, 178, 522/179, 908; 523/109, 115, 116, 118, 300
See application file for complete search history.

(56) References Cited

U.S. PATENT DOCUMENTS

| | | | | |
|---|---|---|---|---|
| 4,966,934 A * | 10/1990 | Huang et al. | ................ | 524/315 |
| 5,367,002 A * | 11/1994 | Huang et al. | ................ | 523/116 |
| 5,749,733 A * | 5/1998 | Qian et al. | ................ | 433/228.1 |
| 5,932,627 A * | 8/1999 | Blackwell | .................... | 523/118 |
| 6,001,897 A * | 12/1999 | Dickens | ...................... | 523/118 |
| 6,126,922 A | 10/2000 | Rozzi et al. | | |
| 6,147,137 A * | 11/2000 | Jia | .............................. | 523/118 |
| 6,210,759 B1 * | 4/2001 | Dickens | ...................... | 427/516 |
| 6,649,669 B1 * | 11/2003 | Dickens | ....................... | 522/76 |
| 2004/0054028 A1 * | 3/2004 | Hattori | ........................ | 523/118 |
| 2004/0229973 A1 * | 11/2004 | Sang et al. | ................. | 523/118 |

FOREIGN PATENT DOCUMENTS

| | | |
|---|---|---|
| JP | 7-101819 | 4/1995 |
| WO | WO 00/69393 | 11/2000 |

* cited by examiner

*Primary Examiner*—Sanza L. McClendon
(74) *Attorney, Agent, or Firm*—Gerald E. Hespos; Anthony J. Casella

(57) ABSTRACT

The present invention provides a one-bottle dental bonding composition that provides a bonding layer excellent in bonding strength, independent of the skill of the practitioners, and, more preferably, that releases fluoride ion gradually into oral cavity over an extended period of time. The one-bottle dental bonding composition comprises a radical polymerizable monomer (A) having an acidic group in the molecule, another radical polymerizable monomer (B), a photopolymerization initiator (C) and a water-soluble organic solvent (D), and is substantially free of water.

15 Claims, 1 Drawing Sheet

ONE-BOTTLE DENTAL BONDING COMPOSITION

BACKGROUND OF THE INVENTION

1. Field of the Invention

The present invention relates to a dental bonding composition and, in particular, to an one-bottle dental bonding composition which is applied onto tooth without any pretreatment of the surface thereof in advance and still provides an excellent bonding layer in a single step, and/or which releases fluoride ion gradually into the oral cavity over an extended period of time.

2. Description of the Related Art

Commercially available dental bonding agents are mainly classified into two groups, a self-etching type and a wet-bonding type as they are called. In the case of bonding agents in the wet-bonding type, the surface of a tooth is treated or etched beforehand with phosphoric acid in order to raise the bonding strength between the tooth and the object to be bonded, and then, while still wet with water after water cleansing, applied with the bonding agent. Such a procedure makes the bonding agent penetrate into tooth deeply in a manner like natural collagen and provides a thicker resin-containing layer on the tooth surface at the same time.

On the other hand, in the case of the bonding agents in the self-etching type, the tooth surface is thoroughly dried by application of blowing air by an air syringe, and subjected, without any pretreatment as described above, to application of a (weakly acidic) bonding agent having a function as an etching agent, thereby providing an bonding layer on the surface of the tooth. By the use of these self-etching bonding agents, the pretreatment process with phosphoric acid inevitably associated with the wet-bonding agents becomes no more required, reducing the risk of the tooth being excessively etched into by phosphoric acid.

However, these methods described in the prior art have disadvantages in that there were required at least two steps to provide the solid bonding layer connecting the tooth and an object to be bonded, thus reducing the efficiency of the manipulation, and that, especially when the bonding agent consists of two or more separately bottled ingredients, addition of another step for mixing and stirring is inevitable, resulting in a possibly large variation in bonding strength of the resulting bonding layer depending on the skill of the practitioners.

SUMMARY OF THE INVENTION

The present invention has been completed to solve the problems described above, and an object of the present invention is to provide an one-bottle dental bonding composition which is easier to handle, provides constantly an excellent bonding layer independent of the skill of the practitioners.

According to an aspect of this invention, a one-bottle dental bonding composition comprises (A) a radical polymerizable monomer having an acidic group in the molecule, (B) another radical polymerizable monomer, (C) a photopolymerization initiator, and (D) a water-soluble organic solvent, as the essential components.

The bonding composition, turning into more acidic when applied onto the surface of a wet tooth, demineralizes and etches into the tooth, and consequently, requires no such pretreatment as is used in the conventional procedures, and provide an excellent bonding layer between the tooth and the object to be bonded.

According to another aspect of this invention, presented is a method of using the bonding composition, comprising coating the bonding composition on the surface of a tooth of a patient, thereby contacting the bonding composition with water on the tooth surface, polymerizing the bonding composition by light irradiation.

These and other objects, feature and advantages of the present invention will become more apparent from the following detailed description of the preferred embodiments/examples with the accompanying drawings.

DETAILED DESCRIPTION OF THE INVENTION

Figure 1:
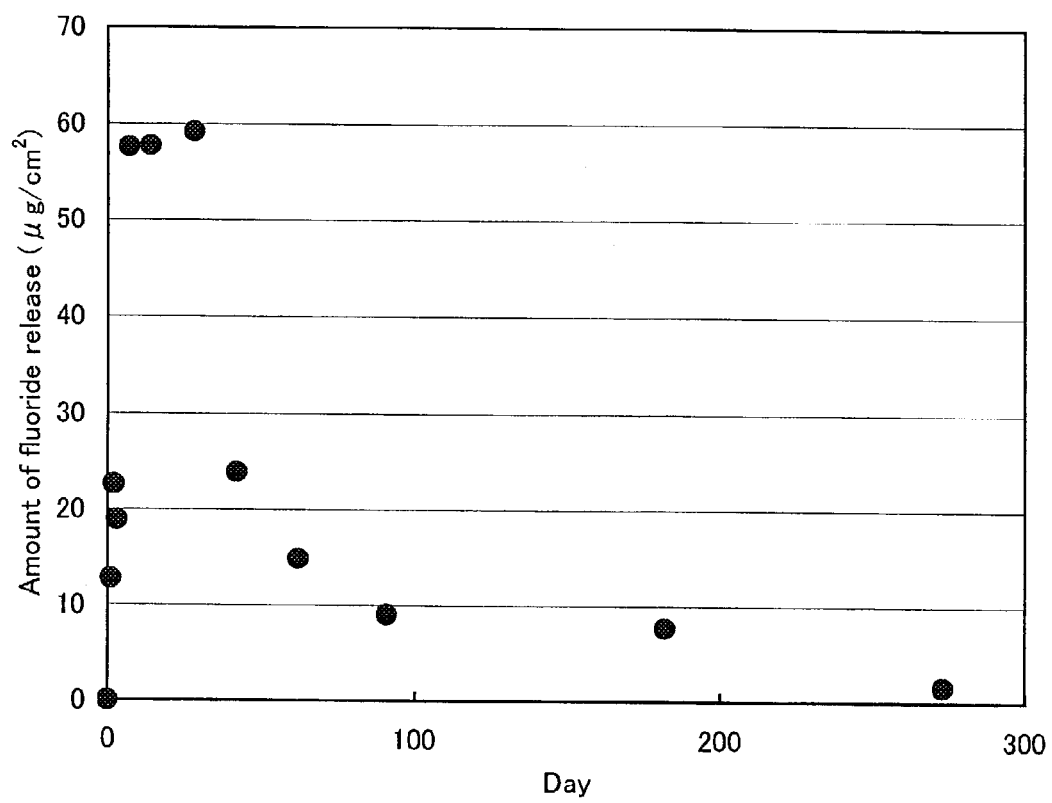
FIG. 1 is a schematic diagram showing the results of evaluation test of fluorine ion release.

A primary feature of the present invention is directed to the one-bottle bonding composition of the present invention comprises (A) a radical polymerizable monomer having an acidic group in the molecule, (B) another radical polymerizable monomer, (C) an photopolymerization initiator, and (D) water-soluble organic solvent, as essential components, and the most advantageous feature thereof is that all components (A), (B) and (C) are dissolved or dispersed in water soluble organic solvent (D), as a one-bottle bonding composition, and thus the resulting bonding composition is applied onto tooth without any pretreatment and yet provides an bonding layer much stronger in the bonding strength. In other words, though the bonding composition of the present invention does not have a high enough acidity as it is to demineralize tooth, but once exposed to water on the surface of the tooth onto which the composition is applied, radical polymerizable monomer (A) therein becomes more acidic by dissociation in the reaction with water, and begins to demineralize the tooth vigorously.

Further, the bonding composition of the present invention is substantially free of water. It is simply because the bonding composition of the present invention contains radical polymerizable monomer (A) which becomes more acidic by contact with water and makes the composition less stable due, for example, to loss of the polymerizable monomers' functionality by the gradual increase in the acidity of radical polymerizable monomer (A) in the presence of water. The water which is contained in bonding composition is less than 1 mass percent, preferably less than 0.5 mass percent, with respect to the bonding composition for the purpose of keeping the stability of the radical polymerizable monomer (A).

Further, another feature of this invention resides in coating the bonding composition on the surface of a tooth of a patient, thereby contacting the bonding composition with water on the tooth surface, polymerizing the bonding composition by light irradiation.

Hereinafter, the present invention will be described in more detail.

First, a radical polymerizable monomer (A) containing an acidic group is an essential component of the bonding composition of the present invention for the purpose of demineralizing teeth. When the bonding composition containing radical polymerizable monomer (A) is applied onto the surface of a tooth, the radical polymerizable monomer (A) becomes more acidic by dissociation in the reaction with water present on the surface of or inside the tooth in the oral cavity and begins to demineralize the tooth. Examples of radical polymerizable monomer (A) are the polymerizable monomers having an acidic group therein, such as carboxylic acid, carboxylic anhydride, phosphoric acid, pyrophosphoric acid, and sulfonic acid.

Typical examples of the radical polymerizable monomer having a carboxylic acid or carboxylic anhydride group in the molecule are 4-(meth)acryloyloxyethoxylcarbonylphthalic acid, 4-(meth)acryloyloxybutyloxylcarbonylphthalic acid, 4-(meth)acryloyloxyhexyloxylcarbonylphthalic acid, 4-(meth)acryloyloxyoctyloxycarbonylphthalic acid, 4-(meth)acryloyloxydecyloxycarbonylphthalic acid, anhydrides of the respective acids above, 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth)acryloyloxy-1,1-undecanedicarboxylic acid, etc.

Typical examples of the radical polymerizable monomer having a sulfonic acid group in the molecule are 2-(meth)acrylamido-2-methylpropane sulfonic acid, styrene sulfonic acid, 2-sulfoethyl(meth)acrylate, etc.

Favorable examples of the radical polymerizable monomer having a phosphoric acid group in the molecule include phosphoric esters of (meth)acrylic acids and pyrophosphoric esters of (meth)acrylic acids. More specifically, the phosphoric esters of (meth)acrylic acids include (meth)acryloyloxymethyl dihydrogen phosphate, 2-(meth)acryloyloxyethyl dihydrogen phosphate, 3-(meth)acryloyloxydipropyl dihydrogen phosphate, 4-(meth)acryloyloxybutyl hydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, di(meth)acryloyloxyethyl hydrogen phosphate, di(meth)acryloyloxybutyl hydrogen phosphate, di(meth)acryloyloxyhexyl hydrogen phosphate, di(meth)acryloyloxyoctyl hydrogen phosphate, di(meth)acryloyloxynonyl hydrogen phosphate, di(meth)acryloyloxydecyl hydrogen phosphate, 1,3-di(meth)acryloyloxypropyl-2-dihydrogen phosphate, 2-(meth)acryloyloxyethyl phenyl hydrogen phosphate, 2-(meth)acryloyloxyethyl 2'-bromoethyl hydrogen phosphate, (meth)acryloyloxyethyl ethyl phenyl phosphate, etc. The pyrophosphoric esters of (meth)acrylic acids include tetra(meth)acryloxyethyl pyrophosphate, di(meth)acryloxylethyl pyrophosphate, etc. Tetramethacryloxyethyl pyrophosphate is most preferable among the compounds above. Further, the compounds described above may be used as a single ingredient or as a mixture of two or more, as radical polymerizable monomer (A).

The bonding composition of the present invention contains another radical polymerizable monomer (B) for the purpose of increasing the functionality as the bonding agent. The radical polymerizable monomer (B) may be either monofunctional or multifunctional compound. Specific examples thereof include hydroxyalkyl(meth)acrylates such as methyl (meth)acrylate, hydroxymethyl (meth)acrylate, hydroxyethyl (meth)acrylate, hydroxypropyl (meth)acrylate, and hydroxybutyl (meth)acrylate,; dimethacrylates having phenyl groups such as ethyleneglycol di(meth)acrylate, di-, tri- or tetraethyleneglycol di(meth)acrylate, di(methacryloxyethyl)trimethylhexamethylene diurethane [generally, abbreviated as UDMA], and 2,2-bis(4-methacryloylethoxylphenyl)propane (Bis-MEPP), carboxylic vinyl esters such as vinyl acetate, vinyl butyrate, and vinyl stearate; and ethylenic unsaturated dicarboxylic acids such as fumaric acid, maleic acid, and itaconic acid. Among the compounds above, hydroxyethyl methacrylate is the most preferable compound.

In another embodiment, the bonding composition of the present invention may further contain another radical polymerizable monomer as component (E) that release fluoride ion, and the component (E) is preferably a phosphazene compound which has a constituent unit represented by the following Formula 1.

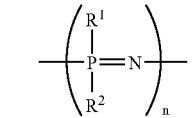

Formula 1

[wherein n in an integer of 3 or 4]

The cyclic phosphazene compound is a most preferable compound as radical polymerizable compound (E) which may be any compound having the constituent unit represented by the chemical formula above, and suitable examples thereof include 6-membered ring compound which is represented by the following Formula 2, and 8-membered ring compounds.

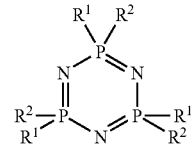

Formula 2

Further, at least one of the groups represented by $R^1$ and $R^2$ in the Formula 1 above is a fluorine atom and the balance are groups having same or different polymerizable double bonds. The groups having polymerizable double bonds are preferably (meth)acryloyloxyalkoxy groups such as 2-(meth)acryloyloxymethoxy, 2-(meth)acryloyloxyethoxy, 2-(meth)acryloyloxypropoxy, and 2-(meth)acryloyloxybutoxy, and more preferably 2-(meth)acryloyloxyethoxy.

Preferable examples of the cyclic phosphazene compound include 6-membered ring compounds having the chemical formula of $P_3N_3(F)_n[O(CH_2)_2OCO(CH_3)C=CH_2]_{6-n}$ (wherein, n is an integer of 1 to 5), 8-membered ring compounds having the chemical formula of $P_4N_4(F)_m[O(CH_2)_2OCO(CH_3)C=CH_2]_{8-m}$ (wherein, m is an integer of 1 to 7), and the like. These compounds are prepared by the reaction of, for example, hydroxyethyl methacrylate with either a 6-membered ring compound having a formula of $P_3N_3F_6$ or a 8-membered ring compound having a formula of $P_4N_4F_8$. The methods for the above reaction are not particularly limited and may be any methods known in the art. For example, the phosphazene compound is prepared in reaction of the starting materials described above in the presence of an organic base such as pyridine, and triethylamine, for removal of hydrogen fluoride, in an organic solvent such as benzene, and toluene, at about 50° C. for 5 to 60 hours.

The cyclic phosphazene compound used as radical polymerizable monomer (E) in the bonding composition of the present invention has, as described above, at least one fluorine atom and radical polymerizable groups in the same molecule. Accordingly, the fluorine-phosphorus bonds of radical polymerizable monomer (E) therein are gradually hydrolyzed by water in saliva- and generate hydrogen fluoride, and thus the composition of the present invention releases fluoride ion into the oral cavity when used as a bonding agent therein. The amount of fluoride ions to be released becomes more remarkable as the content of fluorine atoms in radical polymerizable monomer (E) increases. After release of hydrogen fluoride, the phosphazene compound turns to be more stabilized in the form of P-OH bonds. By polymerization of the polymerizable bonds in the more stabilized phosphazene compound, the composition provides a bonding layer stronger in bonding strength. On the other hand, when both $R^1$ and $R^2$ groups in the cyclic phosphazene compound are fluorine atoms, the compound does not polymerize any more.

The content of radical polymerizable monomers (A) and (B) may vary according to such requirements as viscosity, hardening time, and desired physical properties of the resulting bonding layer, but in the present invention, the content of component (A) is preferably larger, i.e., 50 to 90 parts by mass with respect to 100 parts by mass of the sum of radical polymerizable monomers (A) and (B), since of radical polymerizable monomer (A) is an essential ingredient for the purpose of imparting the bonding composition of the present invention more acidity in the oral cavity. If the content of radical polymerizable monomer (A) is less than 50 parts by mass, such a low content is not sufficient to raise the acidity and thus demineralizing ability of the inventive composition up to such a level as to provide a bonding layer with a satisfactory strong bonding property. The content of component (A) is preferably 60 parts by mass or more, and more preferably 65 parts by mass or more. The upper limit of the same content is preferably 90 parts by mass, for the purpose of keeping an adequate mechanical strength of the resulting bonding layer. The upper limit is preferably 80 parts by mass or less, and much more preferably 70 parts by mass or less.

Radical polymerizable monomer (B) is an ingredient used for increasing reactivity in polymerization and bonding strength of the resulting bonding layer after curing. The content thereof is preferably, but not limited to, 10 to 50 parts by mass.

When component (E) is employed as well as components (A) and (B), the content of component (A) is preferably in the range of 50 to 90 parts by mass with respect to 100 parts by mass of the sum of all radical polymerizable monomers, from the same reason described above. The content is preferably 60 parts by mass or more, and more preferably 65 parts by mass or more. The upper limit of the content of component (A) is about 90 parts by mass, preferably 80 parts by mass or less, and more preferably 75 parts by mass or less.

Radical polymerizable monomer (E) is an ingredient responsible for imparting the bonding composition of the present invention an ability to release fluoride ion gradually. The content of component (E) is preferably 5 to 20 parts by mass, especially for bringing an efficient fluoride releasing capacity sufficient for prevention of dental caries. The content of radical polymerizable monomer (E) is, more preferably, 7 parts by mass or more and 15 parts by mass or less, and, further more preferably, 9 parts by mass or more and 11 parts by mass or less.

In the case above, the content of component (B) is not particularly limited and may be the remainder of the bonding composition which obtained by being subtracting by components (A) and (E).

The bonding composition of the present invention further contains a photopolymerization initiator (C) and/or a photosensitizer (F) in an amount sufficient to carry out polymerization by light irradiation. The content thereof is in a range of 1 to 10 parts by mass with respect to 100 parts by mass of the sum of components (A), (B), and (E). The photopolymerization initiator serves as source of free radicals when irradiated by light. The most preferable as the photopolymerization initiator (C) are redox initiators including tertiary amine reductants. The tertiary amines are not particularly limited insofar as they are used as reductants, and suitable examples thereof include N,N-dimethylamino-p-toluidine, butyldiethanolamine, N,N-dimethylaminoethyl methacrylate, morpholinoethyl methacrylate, ethyl-p-(N,N-dimethylamino)benzoic acid, 2-methacryloxyethyl-p-(N,N-dimethylamino)benzoic acid, dimethylaminobenzoic acid, and esters thereof. The amount of the tertiary amine is preferably in a range of 0.5 to 5 weight percent with respect to the sum of the bonding composition of the present invention.

As the photosensitizer (F), α-diketones may be preferably employed.

Preferable examples of the α-diketones include, but are not limited to, those that are sensitized by irradiation of visible light, such as camphor quinone, benzil, biacetyl, 9,10-phenanthrene quinone and naphthoquinone, and the most preferable is camphor quinone. The content of the photosensitizer (F) is preferably in a range of 0.5 to 2 parts by mass with respect to the bonding composition of the present invention.

The water-soluble organic solvent (D) of the present invention has a role to dissolve or disperse components (A) to (F) described above, and thus to make coating of the bonding composition easier; to facilitate mixing and contact of water in the oral cavity with the components of the present invention on the surface of teeth and to ionize the acidic groups therein, making, as a result, etching of teeth by demineralization easier; and to ensure that the bonding layer formed by polymerization reaction on the surface of teeth has an adequate thickness. Favorable examples of water-soluble organic solvent (D) include alcohols such as ethanol, 1-propanol, isopropyl alcohol, diethylene glycol, and triethylene glycol, ketones such as acetone, and methylethylketone. Ethanol is most preferable from a viewpoint of safety to our body.

The content of the water-soluble organic solvent (D) is not particularly limited insofar as other components in the composition of the present invention can be dissolved or dispersed, but preferably in a range of 20 to 90 parts by mass with respect to 100 parts by mass of the sum of components (A), (B), and (E). As described above, the bonding composition of the present invention, in the presence of water, becomes acidic and begins to etch into the hydroxyapatite layer on the surface of teeth. It is highly likely that the water-soluble organic solvent, with an amount less than 20 parts by mass, may be insufficient to dissolve or disperse other components of the composition, or to increase the potential for demineralization, i.e., etching of teeth surface to a sufficient level. The water-soluble organic solvent, when present in an amount more than 90 parts by mass, makes the resulting bonding composition much less viscous, making the composition flow or ooze away when applied onto teeth. As a result, it becomes more difficult to provide a bonding layer with an appropriate thickness and thus obtain a desired bonding strength. Accordingly, the water-soluble organic solvent (D) is preferably contained in an amount of 30 parts or more by weight and 80 parts by mass or less, and more preferably 40 parts by mass or more and 60 parts by mass or less.

The bonding composition of the present invention may contain a filler to increase hardness and abrasion resistance of the bonding layer after curing and to decrease shrinkage during polymerization and the thermal expansion coefficient of the resulting bonding layer. More specifically, inorganic fillers such as silica, talc, alumina, apatite, glass beads, colloidal silica, barium silicate, and silicon carbide, and organic fillers such as polymethyl(meth)acrylate, are some of the examples of the filler. Silica is recommended as the most preferable filler. The content of the filler is preferably in a range of 0.5 to 2 parts by mass with respect to 100 parts by mass of the sum of components (A), (B), and (E). Alternatively, polymers obtained by prior polymerization of the cyclic phosphazene compounds described above and subsequent hardening may be crushed into particles of a suitable size and used as the organic filler.

Additionally, other components may also be added into the bonding composition of the present invention insofar as they do not have adverse effects on the resulting bonding layer. For example, other polymers such as polyacrylic acid may be added for the purpose of increasing bonding strength, and other materials such as polymerization inhibitors, colorants, UV absorbents and the like may also added if desired.

The bonding composition of the present invention is easily prepared from the components above simply by mixing, and stored in a single container. The container is not particularly limited insofar as it is capable of blocking external light and water. It is favorable that the container is designed in such a manner that the bonding composition therein is easily withdrawn and directly dropped onto the surface of the tooth to be bonded, since it makes coating of the composition in a desired amount.

The one-bottle bonding composition of the present invention is used as a bonding agent or an adhesive cement for regional denture plate resins, rebasing or relining materials thereof, hard resins for tooth crown, filling resins, sealants for prevention of caries, and orthodontic blankets, and/or as an adhesive in a variety of medical applications.

This application is based on Japanese application serial No. 2002-76797 filed in Japan on Mar. 19, 2002, the contents of which are hereby incorporated by reference.

EXAMPLE

Hereinafter, the present invention will be described in more detail with reference to EXAMPLES, but it should be understood that the examples are presented only for the purpose of describing some features of the present invention, and thus the scope of the present invention is not limited thereto. In the following examples, a part means a part by weight unless expressly stated otherwise.

Synthetic Example

Synthesis of Cyclic Phosphazene Compound $P_3N_3F_6$ (hereinafter, referred to as 3PNF) and 2-hydroxyethyl methacrylate (hereinafter, referred to as HEMA) were reacted in toluene at a ratio of 1 to 5 by molar ratio, yielding a cyclic phosphazene compound having polymerizable double bonds.

Preparative Examples 1 to 10

Preparation of Bonding Compositions

Tetramethacryloxyethylpyrophosphoric acid, urethane dimethacrylate, a cyclic phosphazene compound, camphor quinone, ethyl 4-dimethylaminobenzoate, and AEROSIL R-974 (Degussa AG) were dissolved in ethanol to yield bonding compositions 1–10.

TABLE 1

| Component (parts by mass) | Prep. Ex. 1 | Prep. Ex. 2 | Prep. Ex3 | Prep. Ex. 4 | Prep. Ex. 5 |
|---|---|---|---|---|---|
| Tetramethacryloxyethyl-pyropyosphoric acid | 70 | 70 | 70 | 70 | 70 |
| Urethane dimethacrylate | 20 | 20 | 20 | 20 | 20 |
| Cyclic phosphazene compound | 10 | 10 | 10 | 10 | 10 |
| Ethanol | 50 | 0 | 10 | 20 | 100 |
| Camphor quinone | 1 | 1 | 1 | 1 | 1 |
| Ethyl 4-dimethylaminobenzoic | 1 | 1 | 1 | 1 | 1 |
| AEROSIL R-974 | 2 | 2 | 2 | 2 | 2 |
| Component (parts by mass) | Prep. Ex. 6 | Prep. Ex. 7 | Prep. Ex. 8 | Prep. Ex. 9 | Prep. Ex. 10 |
| Tetramethacryloxyethyl-pyropyosphoric acid | 40 | 60 | 80 | 90 | 70 |
| Urethane dimethacrylate | 50 | 30 | 10 | 0 | 30 |
| Cyclic phosphazene compound | 10 | 10 | 10 | 10 | 0 |
| Ethanol | 50 | 50 | 50 | 50 | 50 |
| Camphor quinone | 1 | 1 | 1 | 1 | 1 |
| Ethyl 4-dimethylaminobenzoic | 1 | 1 | 1 | 1 | 1 |
| AEROSIL R-974 | 2 | 2 | 2 | 2 | 2 |

Bonding Test 1

Bonding Strength on Wet Surface (Experiment Nos. 1 to 10)

Bovine anterior tooth were wet polished by the use of silicon carbide abrasive papers #100 and #600 (Nihon Kenshi Co., Ltd) to expose the enamel and dentin surfaces, and then water of these surfaces was blown off by means of a dental air syringe. First, over an enamel or dentin surface of a test piece was placed a cellophane tape with holes, with a diameter of 4 mm, cut open for the identification of the site of bonding test. The tooth surface under the hole was made slightly wet with distilled water, and then brush coated with each of the bonding compositions prepared in PREPARATIVE EXAMPLES 1 to 10, left for 20 seconds and dried slightly by air from the air syringe. On top of each of the bonding layers, a commercially available photopolymerizable dental composite resin, Xeno Paste (DENTSPLY Sankin), was applied. The resin surface was, after covered with another commercial film and additionally a slide glass, pressed and subsequently polymerized and cured by light irradiation for 30 seconds in a visible light polymerizer unit (wave length: 320 to 520 nm, Dentacolor XS, Kulzer). To each of the resulting cured surfaces, a stainless steel rod (diameter: 7 mm, length: 20 mm) was joined by the use of a commercially available dental resin cement, Panapia 21 (Kuraray Co., Ltd). After being left at room temperature for 30 minutes and immersed in water at 37° C. for 24 hours, bonding strength (crosshead speed: 1 mm/min) of the bonding layers was determined. Easiness of applying the bonding compositions was separately determined and classified into three groups and designated as excellent (◎), good (○), and poor (x) The results are summarized in TABLE 2.

of the Experiment Nos. 1 and 4 were superior, and the easiness of applying the bonding compositions was excellent at the same time.

The bonding composition prepared in Preparative Example 2 did not have a sufficiently high bonding strength due to lack of a water-soluble organic solvent (D) which is responsible for the contact of water with component (A) in the bonding composition and for the increase in acidity of the component.

The bonding strength obtained on wet surface in Experiment No. 3 was larger than that obtained on dry surface, but the values of the bonding strength obtained on both the wet and dry surfaces of dentin layer were slightly lower than those in Experiment Nos. 1 and 4. It is presumably because the bonding composition of Experiment No. 3 was low in the content of water-soluble organic solvent (D), leading to a decrease in the contact of water inside the tooth with component (A) in the bonding composition.

Though the bonding strength in Experiment No. 5 was high enough, there was found difficulty in applying the bonding composition due to low viscosity of the composition that contained an excessive amount of water-soluble organic solvent (D).

TABLE 2

| Experiment Number | 1 | 2 | 3 | 4 | 5 | 6 | 7 | 8 | 9 | 10 |
|---|---|---|---|---|---|---|---|---|---|---|
| Bonding agent | Prep. Ex. 1 | Prep. Ex. 2 | Prep. Ex. 3 | Prep. Ex. 4 | Prep. Ex. 5 | Prep. Ex. 6 | Prep. Ex. 7 | Prep. Ex. 8 | Prep. Ex. 9 | Prep. Ex. 10 |
| wet surface Dentin (N/mm$^2$) | 13.3 | 4.5 | 9.4 | 10.5 | 11.4 | 7.4 | 11.5 | 12.6 | 6.5 | 11.5 |
| Enamel (N/mm$^2$) | 19.4 | 10.3 | 13.7 | 14.5 | 16.8 | 12.5 | 15.3 | 16.8 | 10.2 | 15.2 |
| Easiness of application | ◎ | X | X | ○ | X | X | ◎ | ◎ | ○ | ○ |

Bonding Test 2

Bonding Strength on Dry Surface (Experiment Nos. 11 to 15)

Bovine anterior tooth were polished in a similar manner to BONDING TEST 1 and served as samples for the bonding tests. The bonding strength and easiness of applying the bonding compositions were determined according to the method essentially same as that described in BONDING TEST 1, except that the surface of the tooth was not moistened with water before the application of the bonding compositions of Preparative Examples 1 to 5 and thoroughly dried by air from the air syringe. The results are summarized together with those of BONDING TEST 1 in TABLE 3.

The bonding composition in Experiment No. 6, having a smaller amount of component (A), did not have a sufficiently high demineralizing capacity to the tooth, leading to a slightly lower the bonding strength of the resulting bonding layer.

Each of the bonding compositions in Experiment Nos. 7 and 8, although containing a smaller amount of component (A) or (B) than that in Experiment No. 1, gave a bonding layer with an excellent bonding strength.

The bonding composition in Experiment No. 9 gave a bonding layer worse in the mechanical properties as well as the bonding strength due to lack of component (B).

TABLE 3

| Experiment Number | 11 | 12 | 13 | 14 | 15 |
|---|---|---|---|---|---|
| Bonding agent | Prep. Ex. 1 | Prep. Ex. 2 | Prep. Ex. 3 | Prep. Ex. 4 | Prep. Ex. 5 |
| dry surface Dentin (N/mm$^2$) | 9.3 | 4 | 4 | 6.5 | 8.8 |
| Enamel (N/mm$^2$) | 13.5 | 8.3 | 8.8 | 9.2 | 9.8 |
| Easiness of application | ◎ | X | X | ○ | X |

The bonding strengths of the bonding layers formed on the wet surface of tooth in Experiment Nos. 1,3–8 and 10 wherein the bonding compositions used meet the requirements of the present invention were superior than those of the bonding layers formed on the dry surface of tooth in Experiment Nos. 11 to 15. Especially, the bonding strength Alternatively, the bonding composition in Experiment No. 10 did not release fluoride ion due to lack of the cyclic phosphazene compound, even though the bonding strength was excellent.

From the results described above, it may be concluded that a bonding composition that meets the requirements of the present invention provides a bonding layer bound strongly onto a tooth in the wet oral cavity.

Evaluation Test of Fluoride Ion Release

The bonding composition obtained in Preparative Example 1 was immersed in 5 ml of 0.2 M phosphoric acid buffer solution and the daily release of fluoride ion therein was determined. First, the bonding composition of Preparative Example 1 was cured in a metal container to form disk-shaped samples with a diameter of 2 cm and a thickness of 1.5 mm. 5 disks of each of the hardened bonding compositions thus prepared were immersed in 5 ml of 0.2 M phosphoric acid buffer solution. After one day of immersion, the disks were removed and the concentration of fluoride ions in the buffer solution was determined by a fluoride ion electrode (96-09, Orion) and the amount of fluoride ions released during the same day was calculated and expressed in $\mu g/cm^2$-day. The disks were then immersed in another 5 ml solution of fresh 0.2 M phosphoric acid buffer, and the amount of fluoride ions released on the second day was determined in an analogous manner. Similarly, daily release of fluoride ions was determined. The results were shown in FIG. 1.

It is apparent from FIG. 1 that the bonding composition that meets the requirements of the present invention releases fluoride ions gradually over an extended period of time.

INDUSTRIAL APPLICABILITY

A dental bonding composition of the present invention has an excellent ability to etch into and demineralize teeth, can be applied onto teeth without any pretreatment, and thus provides an increased easiness in applying the bonding composition. The bonding composition of the present invention, being a one-bottle composition, provides constantly an excellent bonding layer when applied, independent of the skill of the practitioners. Additionally, the bonding composition releases fluoride ions gradually into the oral cavity over an extended period of time, enabling to prevent dental caries.

Although the present invention has been fully described by way of example with reference to the accompanyings, it is understood that various changes and modification will be apparent to those skilled in the art. Therefore, unless otherwise such changes and modification depart from the scope of the present invention hereinafter defined, they should be construed as being included therein.

What is claimed is:

1. A one-bottle dental self etching bonding composition comprising,
   phosphoric ester and/or pyrophosphoric ester as a radical polymerizable monomer (A) having an acidic group in the molecule thereof, the radical polymerizable monomer (A) being at least one selected from the group consisting of tetra(meth)acryloxyethyl pyrophosphate and di(meth)acryloxylethyl pyrophosphate,
   a radical polymerizable monomer (B),
   a photopolymerization initiator (C),
   and a water-soluble organic solvent (D),
   wherein the bonding composition is substantially free of water, and wherein the bonding composition comprises 20 to 90 parts by mass of said water-soluble organic solvent (D) with respect to 100 parts by mass of the total sum of said radical polymerizable monomers (A) and (B).

2. A one-bottle dental self-etching bonding composition comprising:
   phosphoric ester and/or pyrophosphoric ester as a radical polymerizable monomer (A) having an acidic group in the molecule thereof,
   a radical polymerizable monomer (B),
   a photopolymerization initiator (C),
   a water-soluble organic solvent (D),
   a radical polymerizable monomer (E) which releases fluoride ion,
   wherein the bonding composition is substantially free of water, and wherein the bonding composition comprises 20 to 90 parts by mass of said water-soluble organic solvent (D) with respect to 100 parts by mass of the total sum of said radical polymerizable monomers (A) and (B).

3. A bonding composition according to claim 1, wherein said radical polymerizable monomer (A) has a phosphoric acid group as the acidic group.

4. A bonding composition according to claim 2, wherein the radical polymerizable monomers (A) is at least one selected from the group consisting of tetra(meth)acryloxyethyl pyrophosphate and di(meth)acryloxylethyl pyrophosphate.

5. A bonding composition according to claim 1, wherein radical polymerizable monomer (B) is at least one selected from the group consisting of methyl (meth)acrylate, hydroxymethyl (meth)acrylate, di(methacryloxyethyl)trimethylhexamethylene diurethane, vinyl acetate, fumaric acid, hydroxyethyl methacrylate.

6. A bonding composition according to claim 1, wherein the photopolymerization initiator (C) is at least one selected from the group consisting of N, N-dimethylamino-p-toluidine, butyldiethanolamine, N,N-dimethylaminoethyl methacrylate, morpholinoethyl methacrylate, ethyl-p-(N, N-dimethylamino)benzoic acid.

7. A bonding composition according to claim 1, wherein the water-soluble organic solvent (D) is at least one selected from the group consisting of ethanol, isopropyl alcohol, diethylene glycol.

8. A bonding composition according to claim 1, further comprising a photosensitizer (F).

9. A bonding composition according to claim 1, wherein the bonding composition comprises 50 to 90 parts by mass of said radical polymerizable monomers (A) and 10 to 50 parts by mass of said radical polymerizable monomer (B) with respect to 100 parts by mass of the sum of the radical polymerizable monomers (A) and (B).

10. A bonding composition according to claim 2, wherein the bonding composition comprises 50 to 90 parts by mass of said radical polymerizable monomers (A) and 5 to 20 parts by mass of said radical polymerizable monomer (E), and said (B) as a remainder with respect to 100 parts of the sum of said radical polymerizable monomers (A), (B), and (E).

11. A bonding composition according to claim 1, further comprising a filler (G).

12. A bonding composition according to claim 11, wherein said filler (G) is silica.

13. A method of using a bonding composition comprising coating the bonding composition on the surface of a tooth of a patient, thereby contacting the bonding composition with water on the tooth surface, polymerizing the bonding composition by light irradiation, wherein the bonding composition comprising phosphoric ester and/or pyrophosphoric ester as, a radical polymerizable monomer (A) having anacidic group in the molecule thereof, the radical polymerizable monomer (1) being at least one selected from the group consisting of tetra(meth)acryloxyethyl pyrophosphate and di(meth)acryloxylethyl pyrophosphate, a radical polymerizable monomer (B), a photopolymerization initiator (C), and a water-soluble organic solvent (D), wherein the bonding composition is substantially free of water.

14. A bonding composition according to claim 1, wherein said phosphoric ester is phosphoric ester of (meth)acrylic acid.

15. A bonding composition according to claim 1, wherein said pyrophosphoric ester is pyrophosphoric ester of (meth)acrylic acid.

* * * * *